United States Patent
Paul et al.

(10) Patent No.: US 10,369,551 B2
(45) Date of Patent: Aug. 6, 2019

(54) PRODUCTION OF UNSATURATED CARBOXYLIC ACIDS OR ACID ESTERS WITH A HALOAPATITE-BASED CATALYST

(71) Applicants: ECOLE CENTRALE DE LILLE, Villeneuve D'Ascq (FR); UNIVERSITE DES SCIENCES ET TECHNOLOGIES DE LILLE—LILLE 1, Villeneuve D'Ascq (FR); CENTRE NATIONAL DE LA RECHERCHE SCIENTIFIQUE, Paris (FR)

(72) Inventors: Sébastien Paul, Thun Saint Amand (FR); Benjamin Katryniok, Meurchin (FR); Franck Dumeignil, Villeneuve D'Ascq (FR); Thomas Bonnotte, Paris (FR)

(73) Assignees: ECOLE CENTRALE DE LILLE, Villeneuve d'Ascq (FR); UNIVERSITE DE LILLE, Villeneuve d'Ascq (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 1 day.

(21) Appl. No.: 15/534,291

(22) PCT Filed: Dec. 8, 2015

(86) PCT No.: PCT/FR2015/053369
§ 371 (c)(1),
(2) Date: Jun. 8, 2017

(87) PCT Pub. No.: WO2016/092198
PCT Pub. Date: Jun. 16, 2016

(65) Prior Publication Data
US 2017/0341061 A1    Nov. 30, 2017

(30) Foreign Application Priority Data
Dec. 10, 2014 (FR) .................. 14 62186

(51) Int. Cl.
C07C 51/347 (2006.01)
B01J 27/10 (2006.01)
B01J 27/18 (2006.01)
C07C 51/377 (2006.01)
C01B 25/455 (2006.01)
B01J 37/03 (2006.01)
C07C 57/04 (2006.01)
B01J 27/138 (2006.01)
B01J 27/12 (2006.01)

(52) U.S. Cl.
CPC .......... B01J 27/1806 (2013.01); B01J 37/03 (2013.01); C01B 25/455 (2013.01); C07C 51/377 (2013.01); C07C 57/04 (2013.01); B01J 27/12 (2013.01); B01J 27/138 (2013.01)

(58) Field of Classification Search
CPC ..... C01B 25/455; C07C 51/377; C07C 57/04; C07C 51/347; B01J 27/10; B01J 27/12; B01J 27/1806; B01J 27/138; B01J 37/03
USPC .......... 502/208, 226; 423/308, 462; 554/31; 562/599
See application file for complete search history.

(56) References Cited

U.S. PATENT DOCUMENTS

| 3,658,715 | A | * | 4/1972 | Jones | C09K 11/76 252/301.4 P |
| 4,157,378 | A | * | 6/1979 | Tomlinson | A61K 8/21 423/301 |
| 8,772,539 | B2 | * | 7/2014 | Onda | B01J 21/08 562/599 |
| 9,029,596 | B2 | * | 5/2015 | Yoshida | C07C 51/347 562/512 |
| 2006/0138386 | A1 | * | 6/2006 | McSweeney | C09K 11/7478 252/301.4 H |
| 2008/0033572 | A1 | * | 2/2008 | D'Antonio | A61K 35/32 623/23.51 |
| 2012/0277467 | A1 | | 11/2012 | Onda et al. | |

OTHER PUBLICATIONS

Search Report dated Aug. 7, 2015.
Blanco E et al: "Gas Phase Dehydration of Lactic Acid to Acrylic Acid Over Alkaline-Earth Phosphaes Catalysts," Catalysis Today. Oct. 27, 2013.
Vidfiya C. Ghantani et al: Catalytic Dehydration of Lactic Acid to Acrylic Acide Using Calcium Hydroxyapatite Catalysts, Green Chemistry, Jan. 1, 2013.

* cited by examiner

Primary Examiner — Patricia L. Hailey
(74) Attorney, Agent, or Firm — Troutman Sanders LLP

(57) ABSTRACT

The present invention relates to the use of haloapatites as catalysts of the dehydration reaction of α-hydroxylated carboxylic acids or acid esters, in particular of lactic acid or of methyl lactate, and also to a process for producing unsaturated carboxylic acids or acid esters, in particular acrylic acid or methyl acrylate, in the gas phase in a stainless steel reactor, in the presence of such a catalyst.

10 Claims, No Drawings

PRODUCTION OF UNSATURATED CARBOXYLIC ACIDS OR ACID ESTERS WITH A HALOAPATITE-BASED CATALYST

RELATED APPLICATION

This application is a National Phase of PCT/FR2015/053369, filed on Dec. 8, 2015 which in turn claims the benefit of priority from French Patent Application No. 14 62186, filed on Dec. 10, 2014, the entirety of which are incorporated by reference.

BACKGROUND

Field of the Invention

The present invention relates to the use of haloapatites as catalysts of the dehydration reaction of α-hydroxylated carboxylic acids (or esters), in particular of lactic acid, and also to a process for producing unsaturated carboxylic acids (or esters), in particular acrylic acid, in the gas phase, in the presence of such catalysts.

Description of Related Art

Acrylic acid or acroleic acid or prop-2-enoic acid is an organic compound with the empirical formula $C_3H_4O_2$ and with the semi-structural formula $CH_2=CHCOOH$. Acrylic acid and its esters, the acrylates, are very widely used in industry, in particular in the manufacture of plastics, in acrylic paints and in various other polyacrylics which have multiple uses.

Acrylic acid is generally produced from propylene, which is a by-product derived from fossil resources, in particular from petroleum refining. Specifically, the synthesis of acrylic acid is customarily carried out by gas-phase oxidation, at high temperatures (generally above 350° C.), of propylene in two steps, by passing through acrolein as intermediate product according to the following reactions (1) and (2):

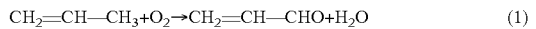  (1)

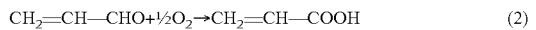  (2)

This process has the drawback of using propylene, the cost price of which is always increasing. Furthermore, during these conversions, various by-products are formed, originating in particular from partial or complete oxidation reactions (acetaldehyde, acetic acid, carbon monoxide, carbon dioxide) and polymerization reactions. To improve the selectivity of the reaction, that is to say to promote the production of acrolein and acrylic acid, it is necessary to use highly selective catalysts. It is also important to be able to have efficient catalysts in order to be able to work at lower temperatures (<400° C.).

Other more recent processes have therefore been developed in order to propose pathways for synthesizing acrylic acid that do not use propylene as raw material. It is in this way that certain processes propose the preparation of acrylic acid by catalytic dehydration of lactic acid according to the following reaction (3):

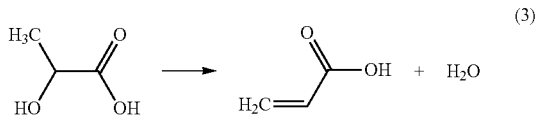  (3)

Thus, in patent application EP 2 495 233, the synthesis of unsaturated carboxylic acids such as acrylic acid is carried out using hydroxycarboxylic acids such as lactic acid, in the gas phase in the presence of a hydroxyapatite-type catalyst in which the Ca/P molar ratio preferably varies from 1.5 to 8 and, in particular, a hydroxyapatite of formula $Ca_{10}(PO_4)_6(OH)_2$ in which the Ca/P molar ratio is 1.67. Although such a process actually makes it possible to carry out the synthesis of unsaturated carboxylic acids, and in particular of acrylic acid, using a raw material derived from biomass, it is carried out in a Pyrex® reactor, that is to say under conditions that are not transposable to the industrial scale where the reactions are generally carried out in stainless steel reactors. Thus, the selectivities that are obtained under laboratory conditions (i.e. in a Pyrex® reactor) could find themselves significantly reduced if the reaction was carried out in a stainless steel reactor. Specifically, patent application US 2013/0274514 proposes a process for preparing acrylic acid by dehydration of lactic acid in the presence of a catalyst based on a mixture of hydrogen phosphates and phosphates. The acrylic acid yield in a quartz reactor is 85% where it is only 58% when the same reaction is carried out under identical operating conditions but this time in a stainless steel reactor. Furthermore, in this patent application US 2013/0274514, a good reproducibility of the catalytic performance is not obtained between two catalysts derived from two identical syntheses.

OBJECTS AND SUMMARY

There is therefore a need for a process for preparing unsaturated carboxylic acids, and in particular acrylic acid, its esters and derivatives, which is independent of propene, while resulting in acrylic acid yields and selectivities that are acceptable when the reaction is carried out in a stainless steel reactor so as to be transposable to the industrial scale. It was during studies on this subject that the present inventors established that halogenated apatites or hydroxyapatites could be used to efficiently catalyze the dehydration reaction of α-hydroxylated carboxylic acids in the gas phase with a very good yield.

The first subject of the present invention is therefore the use of at least one haloapatite of formula (I) below:

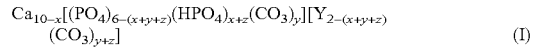  (I)

in which:
Y represents at least one anion selected from the $F^-$, $Cl^-$ anions, and the combinations of at least one $F^-$ or $Cl^-$ anion with an $OH^-$ anion;
$0 \leq x \leq 1$;
$0 \leq y \leq 1$;
$0 \leq z \leq 1$;
$0 \leq x+y+z \leq 1$, as catalyst of the gas-phase dehydration reaction of an α-hydroxylated carboxylic acid or an α-hydroxylated carboxylic acid ester.

According to one preferred embodiment of the invention, the dehydration reaction is carried out on an α-hydroxylated carboxylic acid or acid ester of formula (II) below:

  (II)

in which:

R$^1$ is an alkyl radical having from 1 to 6 carbon atoms, preferably 1 or 2 carbon atoms, and more preferably still 1 carbon atom, R$^2$ represents a hydrogen atom or an alkyl radical having from 1 to 6 carbon atoms; preferably R$^2$ represents a hydrogen atom, a methyl radical or an ethyl radical, and results in an unsaturated carboxylic acid or acid ester of formula (III) below being obtained:

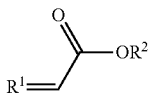
(III)

in which R$^1$ and R$^2$ have the same meaning as in formula (II).

According to one particularly preferred embodiment of the invention, the dehydration reaction is carried out using lactic acid (R$^1$=methyl, R$^2$=H) and results in acrylic acid being obtained.

In particular, in the case of lactic acid, the use of the haloapatites of formula (I) makes it possible to obtain acrylic acid with a better yield (37% approximately for acrylic acid) than by using a non-halogenated hydroxyapatite (29% approximately for acrylic acid), and this in a stainless steel reactor, that is to say under conditions transposable to the industrial scale.

Furthermore, as mentioned above, the α-hydroxylated carboxylic acids and their esters used as raw material, in particular lactic acid and methyl lactate, respectively, may be produced from renewable resources, which makes it possible to avoid fossil resources, and in particular propylene, in order to attain the α-unsaturated carboxylic acids and their corresponding esters and, in particular, acrylic acid.

In the haloapatites of formula (I) above, the Ca/P molar ratio preferably varies from 1.5 to 1.67.

Among the haloapatites of formula (I) above, those in which Y represents an F$^-$ anion or a combination of an F$^-$ anion and an OH$^-$ anion are particularly preferred.

According to one particularly preferred embodiment of the invention, the dehydration reaction is carried out in the presence of a haloapatite of formula (I) in which Y=F; x=0; y=0; z=0 and and of Ca/P molar ratio=1.67.

The specific surface areas of the haloapatites of formula (I), (determined by nitrogen adsorption measurements and calculation by the B.E.T. method), generally vary from 50 to 80 m$^2$/g approximately, but solids with specific surface areas lower and higher than this range may absolutely be applied to this reaction.

The haloapatites of formula (I) in accordance with the invention in which Y= an F$^-$ anion or a combination of an F$^-$ anion and an OH$^-$ anion may be prepared by coprecipitation at basic pH, generally between 9 and 10, of a calcium salt, for example calcium nitrate hexahydrate and of a phosphate, such as, for example, diammonium phosphate, in the presence of ammonium fluoride in molar proportions corresponding, on the one hand, to the desired values of x, y and z and, on the other hand, to the desired Ca/P molar ratio.

The precipitation reaction of the salts at basic pH is preferably carried out at a temperature varying from 65° C. to 80° C. approximately, under stirring, and for a duration of 0.5 to 1 hour approximately.

At the end of the precipitation reaction, the mixture is preferably left under stirring and heating for 5 to 6 hours.

At the end of the synthesis, the haloapatites of formula (I) may be recovered by filtration. They are then washed, oven-dried, then milled before being calcined at a temperature of from 380° C. to 430° C. approximately for 5 to 6 hours approximately.

The haloapatites of formula (I) in accordance with the invention and in which Y= a Cl$^-$ anion or a combination of a Cl$^-$ anion and an OH$^-$ anion may be prepared by precipitation, for example according to the method described by S. Kannan et al., Material Letters., 2006, Volume 60(7), 864-868.

Another subject of the invention consists of a process for producing an unsaturated carboxylic acid or an unsaturated carboxylic acid ester in the presence of a catalyst, characterized in that it comprises at least one step of dehydrating an α-hydroxylated carboxylic acid or an α-hydroxylated carboxylic acid ester, respectively, said step being carried out in the gas phase, in the presence of a solid catalyst containing at least one haloapatite of formula (I) as defined in the first subject of the invention.

According to one preferred embodiment of the invention, the dehydration step is carried out on an α-hydroxylated carboxylic acid or acid ester of formula (II) below:

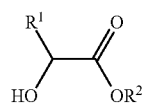
(II)

in which:

R$^1$ is an alkyl radical having from 1 to 6 carbon atoms, preferably 1 or 2 carbon atoms, and more preferably still 1 carbon atom, R$^2$ represents a hydrogen atom or an alkyl radical having from 1 to 6 carbon atoms; preferably R$^2$ represents a hydrogen atom, a methyl radical or an ethyl radical, and results in an unsaturated carboxylic acid or acid ester of formula (III) below being obtained:

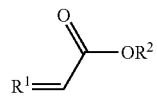
(III)

in which R$^1$ and R$^2$ have the same meaning as in formula (II).

According to one particularly preferred embodiment of the invention, the dehydration reaction is carried out on lactic acid (R$^1$=methyl, R$^2$=H) and results in acrylic acid being obtained.

The catalyst preferably contains a haloapatite of formula (I) in which Y=F$^-$; x=0; y=0; z=0 and the Ca/P molar ratio of which is equal to 1.67.

The dehydration reaction is preferably carried out at a temperature greater than or equal to 300° C. approximately, and more preferably still at a temperature that varies, inclusively, from 350° C. to 400° C. approximately.

According to one preferred embodiment of the process in accordance with the invention, the dehydration reaction is carried out at atmospheric pressure.

Also preferably, the dehydration reaction is carried out in a stainless steel reactor.

The contact time, defined as being the ratio between the volume of catalyst (in mL) and the total volume flow rate of gas injected into the reactor (in mL/s), calculated at the temperature and pressure of the reaction, preferably varies from 0.05 to 2 s approximately, and more preferably still from 0.5 to 1.5 s approximately.

Preferably, the gas phase comprises a carrier gas and/or diluent gas.

The carrier gas and/or diluent gas of the gas phase is preferably an inert gas such as helium or nitrogen.

According to one particular embodiment of the process in accordance with the invention, and even though this is in no case necessary for the correct progression of the dehydration reaction, the haloapatite of formula (I) may be supported by a solid, preferably porous, support. In this case, the solid support may, for example, be selected from supports based on silica, in particular in the form of silica gel (CARiACT® type), mesostructured silica (such as, for example, the mesostructured silica of SBA-15 type), and also from supports based on mixed silica oxides such as, for example, $SiO_2$—$TiO_2$, $SiO_2$—$ZrO_2$, or even from supports of carbide type such as silicon carbide (SiC), etc.

When it is porous, such a solid support preferably has a pore volume of between 0.1 $cm^3/g$ and 2.0 $cm^3/g$ inclusive, and more preferably still between 0.5 $cm^3/g$ and 1.5 $cm^3/g$ inclusive.

When the reaction is finished, the co-products of the reaction may be separated by any appropriate techniques known to a person skilled in the art, for example by distillation.

DETAILED DESCRIPTION

The present invention is illustrated by the following exemplary embodiments, to which it is not however limited.

EXAMPLES

In the following examples, the following raw materials were used:
  diammonium phosphate,
  ammonium fluoride,
  calcium nitrate,
  aqueous ammonia,
  lactic acid.

All these raw materials were obtained from Sigma Aldrich and GPR Rectapure Prolabo, and used as received from the manufacturer, without additional purification.

From these raw materials, haloapatites of formula (I) with Y=F, x=0 and various fluorine contents were prepared.

The fluorine content in the final catalyst is determined by the molar amount of ammonium fluoride used during the synthesis relative to the molar amounts of ammonium phosphate and calcium nitrate introduced.

The synthesis of acrylic acid from lactic acid was carried out in the gas phase in a fixed-bed stainless steel tubular reactor having an internal diameter of 16 mm (external diameter 25 mm) and a length of 178 mm. The injection of the lactic acid was carried out using a high performance liquid chromatography (HPLC) pump sold under the trade name 305 Pump by the company GILSON. The temperature of the reactor was regulated in a precise and controlled manner by a type K thermocouple.

Example 1

Synthesis of a Fluoroapatite of Formula $Ca_{10}(PO_4)_6F_2$ in Accordance with the Invention Carried out in this example was the synthesis of a haloapatite of formula (I) in accordance with the invention in which Y=F, x=0, y=0 and z=0 and of which the theoretical Ca/P molar ratio in solution is equal to 1.67. The empirical formula of the catalyst in this case is $Ca_{10}(PO_4)_6F_2$.

A 0.1M solution of diammonium phosphate in water and containing 33.4 mmol of ammonium fluoride was brought, with stirring, to a temperature of 65° C. in a polytetrafluoroethylene (PTFE) container. The pH of the solution was adjusted to 9 and maintained at this value before and during the precipitation, by adding a 28 wt % solution of aqueous ammonia.

200 mL of an aqueous solution containing 0.167 mol of calcium nitrate were then added dropwise to the solution of diammonium phosphate and ammonium fluoride (in 1 to 2 hours) obtained previously, with stirring and at a temperature between 65° C. and 80° C. Throughout the precipitation, the pH of the mixture was maintained at the initial value by suitable additions of a 28 wt % solution of aqueous ammonia.

At the end of the addition, the mixture was left to cool with stirring for 5 to 6 hours.

The solid that had precipitated was then filtered on a Büchner funnel then washed and filtered a minimum of three times with demineralized hot water. The precipitated solid cake thus obtained was then kept overnight in the oven at 100° C.

On leaving the oven, the recovered solid was finely milled then calcined in a muffle furnace at 400° C. for 5 to 6 hours.

A powder of fluoroapatite of formula $Ca_{10}(PO_4)_6F_2$ was thus obtained.

Example 2

Synthesis of a Hydroxyfluoroapatite of Formula $Ca_{10}(PO_4)_6(OH)F$ in Accordance with the Invention Carried out in this example was the synthesis of a halogenated hydroxyapatite of formula (I) in accordance with the invention in which Y represents a combination of an $F^-$ anion with an $OH^-$ anion, x=0, y=0 and z=0 and of which the theoretical Ca/P molar ratio in solution is equal to 1.67. The empirical formula of the catalyst in this case is $Ca_{10}(PO_4)_6(OH)F$.

The synthesis was carried out according to a procedure identical to that of Example 1 above but using a substoichiometric amount of fluorine, namely 16.7 mmol of ammonium fluoride.

A powder of fluoroapatite of formula $Ca_{10}(PO_4)_6(OH)F$ was thus obtained.

Comparative Example 3

Synthesis of a Non-Halogenated Hydroxyapatite of Formula $Ca_{10}(PO_4)_6(OH)_2$ not in Accordance with the Invention Carried out in this example was the synthesis of a non-halogenated hydroxyapatite that is not part of the invention and that has the formula $Ca_{10}(PO_4)_6(OH)_2$.

The synthesis was carried out according to a procedure identical to that of Example 1 above, at a temperature of 85° C. and at pH 10, and by using a diammonium phosphate solution that does not comprise ammonium fluoride, all the other reactants being used in the same molar amounts as in Example 1.

A powder of hydroxyapatite of formula $Ca_{10}(PO_4)_6(OH)_2$ was thus obtained.

Example 4

Synthesis of Acrylic Acid from Lactic Acid

Tested in this example were the catalytic properties of a fluoroapatite and of a hydroxyfluoroapatite in accordance with the invention and as respectively prepared according to Examples 1 and 2 above, in comparison with those of the non-halogenated hydroxyapatite not in accordance with the invention and as prepared above according to comparative Example 3.

The general procedure followed was the following: 1 g of milled catalyst was placed in the stainless steel fixed-bed reactor and held in the middle of the reactor on a quartz wool bed, itself held by stainless steel metal foam. The reactor thus loaded was heated at the dehydration reaction temperature of the lactic acid, that is to say between 350° C. and 375° C.

A 25 wt % aqueous solution of lactic acid was injected using the HPLC pump, at a flow rate of from 1.5 mL/h to 6 mL/h into an injection chamber heated at 190° C. The evaporation of the lactic acid solution was carried out under a flow of helium with a flow rate of from 15 mL/min to 30 mL/min. The lactic acid supply was stabilized overnight before the start of the catalytic test.

During the catalytic tests, the liquids flowing out of the reactor were immediately condensed in a water-filled glass trap immersed in a cryostatically controlled bath at 4° C. The condensate was analyzed every 1 h 30 min by gas chromatography equipped with a flame ionization detector.

The conversion and selectivity calculations were carried out in the following manner:

Conversion C %=[(moles of lactic acid injected)−(moles of lactic acid analyzed at the outlet)/(moles of lactic acid injected)]×100

Acrylic acid selectivity S. AA %=[(moles of acrylic acid analyzed at the outlet)/(moles of lactic acid converted)]×100.

The results of the catalytic tests carried out with the hydroxyapatite not in accordance with the invention and synthesized according to comparative Example 3, with the fluoroapatite in accordance with the invention and as prepared according to Example 1 and with the hydroxyfluoroapatite in accordance with the invention and as prepared according to Example 2 are presented in Tables I and II below:

TABLE I

| Catalyst | C % | S. AA % | Yield % |
|---|---|---|---|
| $Ca_{10}(PO_4)_6(OH)_2$ (Ex. 3) | 97 | 30 | 29.1 |
| $Ca_{10}(PO_4)_6F_2$ (Ex. 1) | 100 | 37 | 37.0 |

Reaction temperature: 350° C.; 25 wt % lactic acid solution; flow rate of the lactic acid solution: 1.5 mL/h, helium flow rate: 15 mL/min.

TABLE II

| Catalyst | C % | S. AA % | Yield % |
|---|---|---|---|
| $Ca_{10}(PO_4)_6(OH)_2$ (Ex. 3) | 93.4 | 34.3 | 32.0 |
| $Ca_{10}(PO_4)_6(OH)F$ (Ex. 2) | 93.3 | 36.1 | 33.7 |
| $Ca_{10}(PO_4)_6F_2$ (Ex. 1) | 99 | 38.5 | 38.1 |

Reaction temperature: 375° C.; 25 wt % lactic acid solution; flow rate of the lactic acid solution: 6 mL/h, helium flow rate: 30 mL/min.

The results from Tables I and II show that the apatites and hydroxyapatites containing fluorine, and in accordance with the present invention, make it possible to obtain better yields of acrylic acid than the non-halogenated reference hydroxyapatite, under given operating conditions.

All of the results presented in this invention, under various conditions, demonstrate that haloapatites tested for the dehydration of lactic acid to give acrylic acid are efficient and selective for acrylic acid, and this being under conditions transposable to the industrial scale.

The invention claimed is:

1. Process for producing an unsaturated carboxylic acid or an unsaturated carboxylic acid ester in the presence of a catalyst, said process comprising the steps of:
   dehydrating an α-hydroxylated carboxylic acid or an α-hydroxylated carboxylic acid ester, respectively, said step being carried out in the gas phase, in the presence of a solid catalyst containing at least one halogenated apatite of formula (I) below:

$$Ca_{10-x}[(PO_4)_{6-(x+y+z)}(HPO_4)_{x+z}(CO_3)_3][Y_{2-(x+y+z)}(CO_3)_{y+z}] \quad (I)$$

in which:
   Y represents at least one anion selected from the $F^-$, $Cl^-$ anions, and the combinations of at least one $F^-$ or $Cl^-$ anion with an $OH^-$ anion;
   $0 \leq x \leq 1$;
   $0 \leq y \leq 1$;
   $0 \leq z \leq 1$;
   $0 \leq x+y+z \leq 1$,
said process being carried out in a stainless steel reactor.

2. The process according to claim 1, wherein the dehydration step is carried out on an α-hydroxylated carboxylic acid or acid ester of formula (II) below:

(II)

in which:
   $R^1$ is an alkyl radical having from 1 to 6 carbon atoms,
   $R^2$ represents a hydrogen atom or an alkyl radical having from 1 to 6 carbon atoms;
and results in an unsaturated carboxylic acid or acid ester of formula (III) below being obtained:

(III)

in which $R^1$ and $R^2$ have the same meaning as in formula (II).

3. The process according to claim 2, wherein the dehydration step is carried out on an α-hydroxylated carboxylic acid or acid ester of formula (II) in which R1 is an alkyl radical having 1 carbon atom and R2 represents a hydrogen atom, a methyl radical or an ethyl radical.

4. The process according to claim 1, wherein the dehydration step is carried out using lactic acid and rests in acrylic acid being obtained.

5. The process according to claim 1, wherein the catalyst contains at least one halogenated apatite of formula (I) in which Y=F$^-$; x=0; y=0; z=0 and of Ca/P molar ratio=1.67.

6. The process according to claim 1, wherein the dehydration reaction is carried out at a temperature greater than or equal to 300° C.

7. The process according to claim 1, wherein the dehydration reaction is carried out at atmospheric pressure.

8. The process according to claim 1, wherein the gas phase comprises a carrier gas and/or diluent gas.

9. The process according to claim 8, wherein the carrier gas and/or diluent gas of the gas phase is an inert gas selected from helium and nitrogen.

10. The process according to claim 1, wherein the halogenated apatite of formula (I) is supported by a solid support.

* * * * *